(12) United States Patent
Niu et al.

(10) Patent No.: US 7,593,119 B2
(45) Date of Patent: *Sep. 22, 2009

(54) GENERATION OF A LIBRARY OF PERIODIC GRATING DIFFRACTION SIGNALS

(75) Inventors: Xinhui Niu, San Jose, CA (US); Nickhil Jakatdar, Los Altos, CA (US)

(73) Assignee: Tokyo Electron Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/866,408

(22) Filed: Oct. 2, 2007

(65) Prior Publication Data

US 2008/0249754 A1    Oct. 9, 2008

Related U.S. Application Data

(63) Continuation of application No. 11/189,161, filed on Jul. 25, 2005, now Pat. No. 7,277,189, which is a continuation of application No. 09/907,488, filed on Jul. 16, 2001, now Pat. No. 6,943,900.

(60) Provisional application No. 60/233,017, filed on Sep. 15, 2000.

(51) Int. Cl.
    *G01B 11/14* (2006.01)

(52) U.S. Cl. .................................. 356/625; 356/630

(58) Field of Classification Search ............... 356/625, 356/328, 601, 630; 702/57, 66, 81, 155, 702/166, 189; 703/6

See application file for complete search history.

(56) References Cited

U.S. PATENT DOCUMENTS

| | | | |
|---|---|---|---|
| 5,599,594 A | 2/1997 | Pauley | |
| 5,963,329 A | 10/1999 | Conrad et al. | |
| 6,049,762 A * | 4/2000 | Ganz et al. | 702/104 |
| 6,091,486 A | 7/2000 | Kirk | |
| 6,657,736 B1 * | 12/2003 | Finarov et al. | 356/625 |
| 6,943,900 B2 | 9/2005 | Niu et al. | |
| 7,277,189 B2 | 10/2007 | Niu et al. | |

FOREIGN PATENT DOCUMENTS

| | | |
|---|---|---|
| DE | 19636612 A1 | 3/1998 |
| WO | WO-02/23231 A2 | 3/2002 |

OTHER PUBLICATIONS

Doddi, S. R. et al. (Jul. 2000). "Approximation Algorithms for Clustering to Minimize the Sum of Diameters," *Scandinavian Workshop on Algorithm Theory (SWAT)*, Bergen, Norway, 20 pages.

(Continued)

*Primary Examiner*—Roy Punnoose

(57) ABSTRACT

A method of generating a library of simulated-diffraction signals (simulated signals) of a periodic grating includes obtaining a measured-diffraction signal (measured signal). Hypothetical parameters are associated with a hypothetical profile. The hypothetical parameters are varied within a range to generate a set of hypothetical profiles. The range to vary the hypothetical parameters is adjusted based on the measured signal. A set of simulated signals is generated from the set of hypothetical profiles.

30 Claims, 9 Drawing Sheets

OTHER PUBLICATIONS

Forouhi, A. R. et al. (Jul. 15, 1988). "Optical Properties of Crystalline Semiconductors and Dielectrics," *Physical Review B* 38(3):1865-1874.

Gaylord, T. K. et al. (May 1985). "Analysis and Applications of Optical Diffraction by Gratings," *Proceedings of the IEEE* 73(5):894-904.

Jakatdar, N. et al. (Mar. 1999) "A Parameter Extraction Framework for DUV Lithography Simulation," *SPIE Conference on Metrology, Inspection and Process Control for Microlithography XIII*, Santa Clara, California, 3677:447-456.

Jellison, G. E. et al. (Jul. 15, 1996). "Parameterization of the Optical Functions of Amorphous Materials in the Interband Region," *Applied Physics Letters* 69(3):371-373.

Naqvi, S. S. H. et al. (Sep. 1994). "Etch Depth Estimation of Large-Period Silicon Gratings with Multivariate Calibration of Rigorously Simulated Diffraction Profiles," *Journal of the Optical Society of America A* 11(9):2485-2493.

Neter, J. et al. (1982). *Applied Statistics*, 2nd Edition, Allyn and Bacon: Boston, Massachusetts, 10 pages. (Table of Contents).

Niu, X. et al. (1998). "Novel DUV Photoresist Modeling by Optical Thin-Film Decomposition from Spectral Ellipsometry/Reflectometry Data," *SPIE LASE*, 8 pages.

Niu, X. et al. (Apr. 20, 1999). "An Integrated System of Optical Metrology for Deep Sub-Micron Lithography," PhD Dissertation, Electronics Research Lab, College of Engineering, UC Berkeley, CA, 155 pages.

Niu, X. (May 1999). "Deep Ultraviolet Lithography Simulator Tuning by Resist Profile Matching," *EUROPTO Conference on Lithography for Semiconductor Manufacturing*, Edinburgh, Scotland, 8 pages.

Press, W. H. et al. (1988). "Simulated Annealing Methods" Chapter 10.9 *In Numerical Recipes in C: The Art of Scientific Computing*. Cambridge University Press: Cambridge, New York, pp. 444-455.

U.S. Appl. No. 09/764,780, filed Jan. 17, 2001 for Niu et al.

* cited by examiner

GENERATION OF A LIBRARY OF PERIODIC GRATING DIFFRACTION SIGNALS

CROSS REFERENCE TO RELATED APPLICATION

This application is a continuation of U.S. application Ser. No. 11/189,161, filed Jul. 25, 2005, which is a continuation of U.S. application Ser. No. 09/907,488, filed Jul. 16, 2001, now issued as U.S. Pat. No. 6,943,900, which claims the benefit of earlier filed U.S. Provisional Application Ser. No. 60/233,017, filed on Sep. 15, 2000, the entire contents of which are incorporated herein by reference for all purposes.

BACKGROUND OF THE INVENTION

1. Field of the Invention

The present application generally relates to generating simulated-diffraction signals/signals for periodic gratings. More particularly, the present application relates to generating a library of simulated-diffraction signals indicative of electromagnetic signals diffracting from periodic gratings.

2. Description of the Related Art

In semiconductor manufacturing, periodic gratings are typically used for quality assurance. For example, one typical use of periodic gratings includes fabricating a periodic grating in proximity to the operating structure of a semiconductor chip. The periodic grating is then illuminated with an electromagnetic radiation. The electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional system, the diffraction signal collected from illuminating the periodic grating (the measured-diffraction signal) is compared to a library of simulated-diffraction signals. Each simulated-diffraction signal in the library is associated with a theoretical profile. When a match is made between the measured-diffraction signal and one of the simulated-diffraction signals in the library, the theoretical profile associated with the simulated-diffraction signal is presumed to represent the actual profile of the periodic grating.

The accuracy of this conventional system depends, in part, on the range and/or resolution of the library. More particularly, the range of the library relates to the range of different simulated-diffraction signals in the library. As such, if the collected-diffraction signal is outside of the range of the library, then a match cannot be made. The resolution of the library relates to the amount of variance between the different simulated-diffraction signals in the library. As such, a lower resolution produces a coarser match.

Therefore, the accuracy of this convention system can be increased by increasing the range and/or resolution of the library. However, increasing the range and/or the resolution of the library also increases the amount of computations required to generate the library. As such, it is desirable to determine an appropriate range and/or resolution for the library without unduly increasing the amount of computations required.

SUMMARY

The present application relates to generating a library of simulated-diffraction signals (simulated signals) of a periodic grating. In one embodiment, a measured-diffraction signal of the periodic grating is obtained (measured signal). Hypothetical parameters are associated with a hypothetical profile. The hypothetical parameters are varied within a range to generate a set of hypothetical profiles. The range to vary the hypothetical parameters is adjusted based on the measured signal. A set of simulated signals is generated from the set of hypothetical profiles.

DESCRIPTION OF THE DRAWING FIGURES

The present invention can be best understood by reference to the following description taken in conjunction with the accompanying drawing figures, in which like parts may be referred to by like numerals:

DETAILED DESCRIPTION

The following description sets forth numerous specific configurations, parameters, and the like. It should be recognized, however, that such description is not intended as a limitation on the scope of the present invention, but is instead provided to provide a better description of exemplary embodiments.

Figure 1:
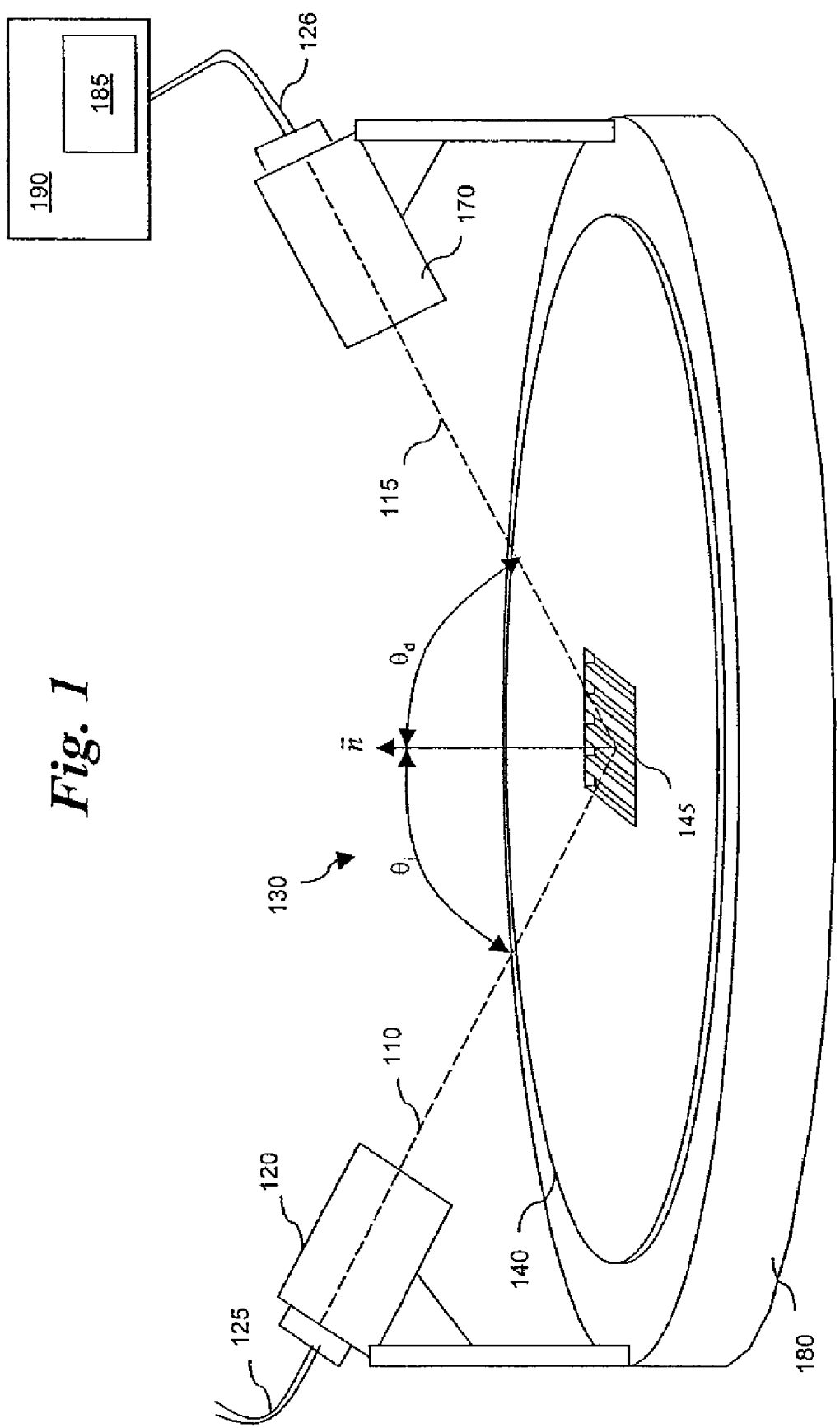
FIG. 1 is a perspective view of a system for illuminating a periodic grating with an incident signal and detecting deflection signals from the periodic grating.

With reference to FIG. 1, a periodic grating 145 is depicted on a semiconductor wafer 140. As depicted in FIG. 1, wafer 140 is disposed on a process plate 180, which can include a chill plate, a hot plate, a developer module, and the like. Alternatively, wafer 140 can also be disposed on a wafer track, in the end chamber of an etcher, in an end-station or metrology station, in a chemical mechanical polishing tool, and the like.

As described earlier, periodic grating 145 can be formed proximate to or within an operating structure formed on wafer 140. For example, periodic grating 145 can be formed adjacent a transistor formed on wafer 140. Alternatively, periodic grating 145 can be formed in an area of the transistor that does not interfere with the operation of the transistor. As will be described in greater detail below, the profile of periodic grating 145 is obtained to determine whether periodic grating 145, and by extension the operating structure adjacent periodic grating 145, has been fabricated according to specifications.

More particularly, as depicted in FIG. 1, periodic grating 145 is illuminated by an incident signal 110 from an electromagnetic source 120, such as an ellipsometer, reflectometer, and the like. Incident signal 110 is directed onto periodic grating 145 at an angle of incident $\theta_i$ with respect to normal $\vec{n}$ of periodic grating 145. Diffraction signal 115 leaves at an angle of $\theta_d$ with respect to normal $\vec{n}$. In one exemplary embodiment, the angle of incidence $\theta_i$ is near the Brewster's angle. However, the angle of incident $\theta_i$ can vary depending on the application. For example, in an alternative embodiment, the angle of incident $\theta_i$ is between about 0 and about 40 degrees. In another embodiment, the angle of incident $\theta_i$ is between about 30 and about 90 degrees. In still another embodiment, the angle of incident $\theta_i$ is between about 40 and about 75 degrees. In yet another embodiment, the angle of incident $\theta_i$ is between about 50 and about 70 degrees.

Diffraction signal 115 is received by detector 170 and analyzed by signal-processing system 190. When electromagnetic source 120 is an ellipsometer, the magnitude $\Psi$ and the phase $\Delta$ of diffraction signal 115 is received and detected. When electromagnetic source 120 is a reflectometer, the relative intensity of diffraction signal 115 is received and detected.

Signal-processing system 190 compares the diffraction signal received by detector 170 to simulated-diffraction signals stored in a library 185. Each simulated-diffraction signal in library 185 is associated with a theoretical profile. When a match is made between the diffraction signal received from detector 170 and one of the simulated-diffraction signals in library 185, the theoretical profile associated with the matching simulated-diffraction signal is presumed to represent the actual profile of periodic grating 145. The matching simulated-diffraction signal and/or theoretical profile can then be provided to assist in determining whether the periodic grating has been fabricated according to specifications.

Figure 11:
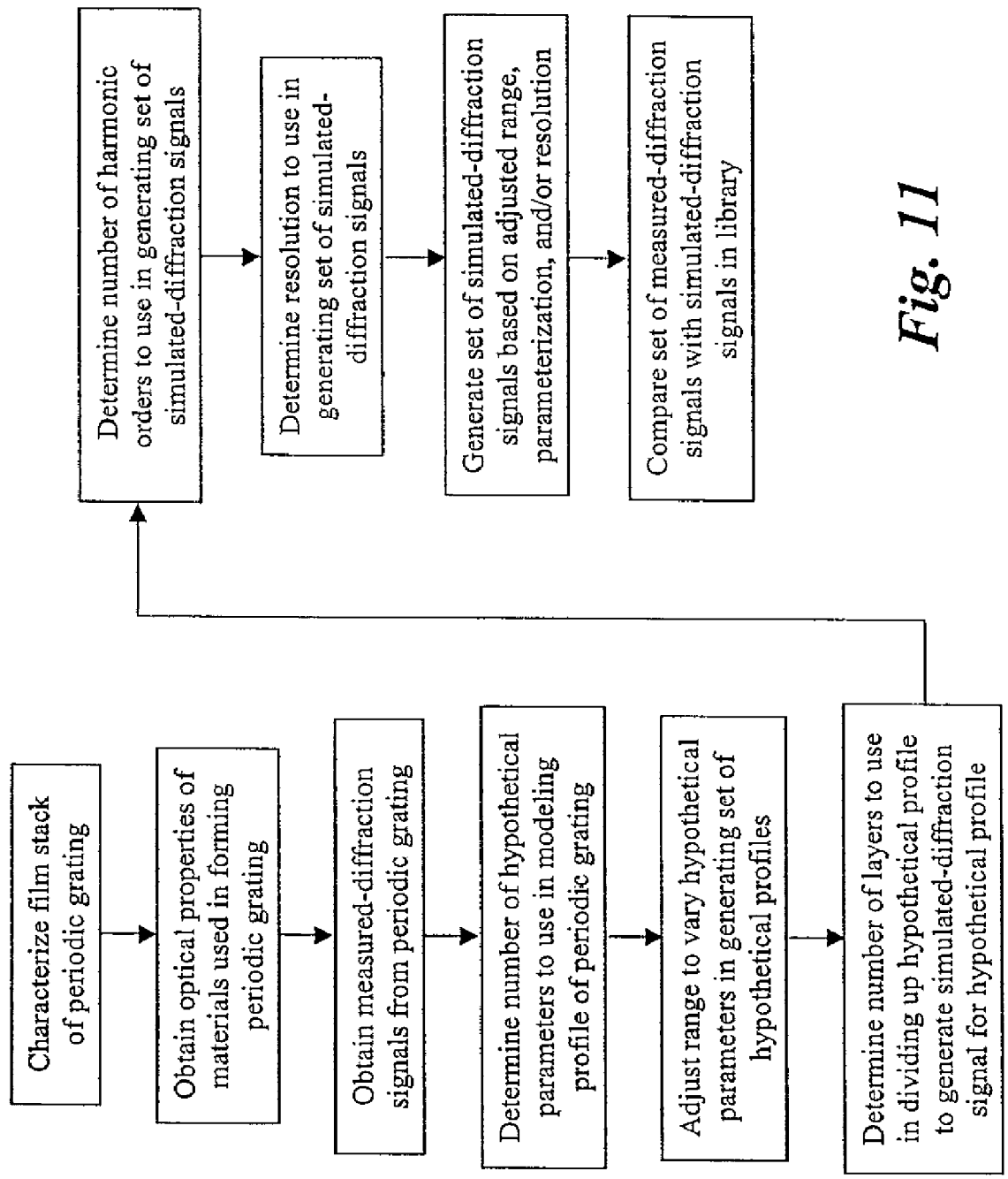
FIG. 11 is a flow chart of an exemplary library generation process.

As described above, library 185 includes simulated-diffraction signals that are associated with theoretical profiles of periodic grating 145. As depicted in FIG. 11, in the present exemplary embodiment, the process for generating library 185 can include: (1) characterizing the film stack of the periodic grating; (2) obtaining the optical properties of the materials used in forming the periodic grating; (3) obtaining measured-diffraction signals from the periodic grating; (4) determining the number of hypothetical parameters to use in modeling the profile of the periodic grating; (5) adjusting the range to vary the hypothetical parameters in generating a set of hypothetical profiles; (6) determining the number of layers to use in dividing up a hypothetical profile to generate a simulated-diffraction signal for the hypothetical profile; (7) determining the number of harmonic orders to use in generating the set of simulated-diffraction signals; (8) determining a resolution to use in generating the set of simulated-diffraction signals; (9) generating the set of simulated-diffraction signals based on the adjusted range, parameterization, and/or resolution; and (10) comparing a set of measured-diffraction signals with the simulated-diffraction signals in the library.

With reference to FIG. 1, the process outlined above and described in greater detail below for generating library 185 can be performed by signal-processing system 190. Additionally, although signal-processing system 190 and detector 170 and electromagnetic source 120 are depicted being connected by lines 126 and 125, data can be communicated between signal-processing system 190 and detector 170 and electromagnetic source 120 through various methods and media. For example, data can be communicated using a diskette, a compact disk, a phone line, a computer network, the Internet, and the like.

Furthermore, it should be noted that the process outlined above for generating library 185 is meant to be exemplary and not exhaustive or exclusive. As such, the process for generating library 185 can include additional steps not set forth above. The process for generating library 185 can also include fewer steps than set forth above. Additionally, the process for generating library 185 can include the steps set forth above in a different order. With this in mind, the exemplary process outlined above is described in greater detail below:

1. Characterizing the Film Stack of the Periodic Grating:

With continued reference to FIG. 1, prior to generating library 185, characteristics of periodic grating 145 are obtained. For example, the following information can be acquired:

Specifics of the measurement tool to be used, such as the incident angle and wavelength range of the illuminating incident signal 110.

The materials used in forming periodic grating 145 and which of the layers in the stack are patterned.

A range for each of the parameters for periodic grating 145, such as the thickness in the case of un-patterned layers, or the width (i.e., "critical dimension" or "CD") and thickness in the case of patterned layers.

A desired resolution for the critical dimension in the case of patterned films.

A pitch, i.e., periodicity length, of patterned-film periodic grating 145.

A specification of the type of expected profile shapes, such as "footings", "undercuts", and the like.

These characteristics of periodic grating 145 can be obtained based on experience and familiarity with the process. For example, these characteristics can be obtained from a process engineer who is familiar with the process involved in fabricating wafer 140 and periodic grating 145. Alternatively, these characteristics can be obtained by examining sample periodic gratings 145 using Atomic Force Microscope (AFM), tilt-angle Scanning Electron Microscope (SEM), X-SEM, and the like.

2. Obtaining the Optical Properties of the Materials Used in Forming the Periodic Grating.

Figure 2:
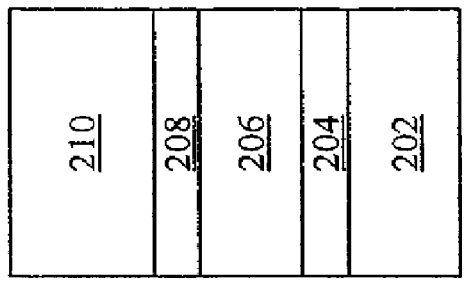
FIG. 2 is a cross-sectional view of a portion of a periodic grating having multiple layers.

In the present exemplary embodiment, the optical properties of the materials used in forming the periodic grating are obtained by measuring diffraction signals. With reference to FIG. 2, assume for example that a sample periodic grating includes four layers (i.e., layers 204, 206, 208, and 210) of different materials formed on a substrate 202. Assume for example that layers 204, 206, 208, and 210 are Gate Oxide, Polysilicon, Anti-reflective coating, and Photoresist, respectively, and that substrate 202 is Silicon.

Figure 3:
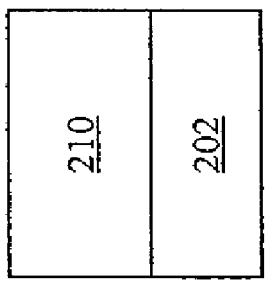
FIG. 3 is a cross-sectional view of the multiple layers of the periodic grating in FIG. 2 being formed separately on the substrate of the periodic grating in FIG. 2.
Figure 3:
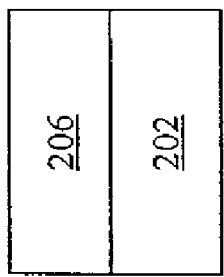
Figure 3:
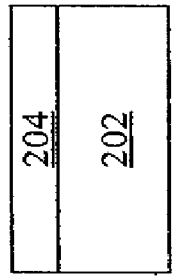

As depicted in FIG. 3, the optical properties of each material can be obtained by measuring a separate diffraction signal for each layer 204, 206, 208, and 210 formed on substrate 202. More particularly, a diffraction signal is measured for layer 204 formed on substrate 202. A separate diffraction signal can be measured for layer 206 formed on substrate 202. Another separate diffraction signal can be measured for layer 208 formed on substrate 202. And yet another separate diffraction signal can be measured for layer 210 formed on substrate 202.

Figure 4:
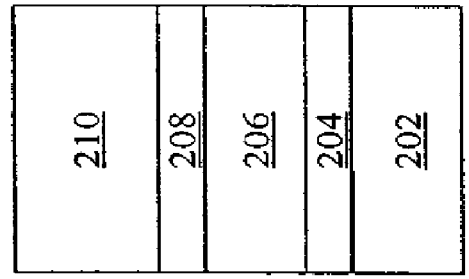
FIG. 4 is a cross-sectional view of the multiple layers of the periodic grating in FIG. 2 being formed sequentially on the substrate of the periodic grating in FIG. 2.
Figure 4:
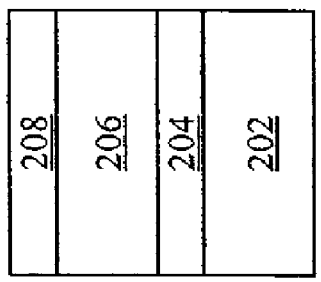
Figure 4:
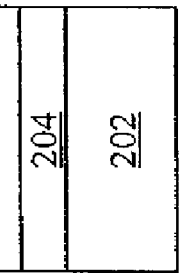
Figure 4:
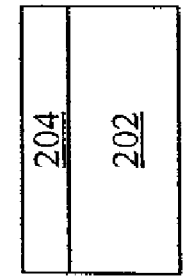

Alternative, as depicted in FIG. 4, in accordance with what is herein referred to as the "Additive Stack" approach, diffraction signals are measured as layers 204, 206, 208, and 210 are sequentially formed on top of substrate 202. More particularly, a diffraction signal is measured after forming layer 204 on substrate 202. Another diffraction signal is measured after forming layer 206 on layer 204. Still another diffraction signal is measured after forming layer 208 on layer 206. Yet another diffraction signal is measured after forming layer 210 on layer 208.

With reference again to FIG. 1, after measuring the diffraction signals for each material used to form periodic grating 145, the optical properties for each material is extracted. More particularly, with reference again to FIG. 2, assuming for example that periodic grating 145 (FIG. 1) includes layers 204 through 210 formed on substrate 202, the optical properties of each layer 204 through 210 are extracted. In the present exemplary embodiment, the real and imaginary parts (n and k) of the refractive index of each layer 204 through 210 are extracted using an optimizing engine in conjunction with a thin film electromagnetic equation solver. For example, the refractive index can be extracted using a simulated annealing based optimizer, herein referred to as a Simulated Annealing for Continuous (SAC) variables optimizer.

When layers 204 through 210 include a metal layer, which is highly reflective, the incident signal 110 (FIG. 1) may only penetrate the metal layer to a "skin depth" of typically a few nanometers. Hence, only the n-k can be extracted, while the nominal thickness value are not measured but obtained theoretically or based on experience, such as from a process engineer.

For non-metal layers, a variety of physical models can be used in conjunction with the SAC optimizer to extract the optical properties, including the thickness, of the films. For examples of suitable physical models, see G. E. Jellison, F. A. Modine, "Parameterization of the optical functions of amorphous materials in the interband region", Applied Physics Letters, 15 vol 69, no. 3, 371-373, July 1996, and A. R. Forouhi, I. Bloomer, "Optical Properties of crystalline semiconductors and dielectrics", Physical Review B., vol. 38, no. 3, 1865-1874, July 1988, the entire content of which is incorporated herein by reference.

Additionally, when an ellipsometer is used to obtain the diffraction signals, the logarithm of the tan ($\Psi$) signal and the cos ($\Delta$) signal can be compared (as is described in "Novel DUV Photoresist Modeling by Optical Thin-Film Decompositions from Spectral Ellipsometry/Reflectometry Data," SPIE LASE 1998, by Xinhui Niu, Nickhil Harshvardhan Jakatdar and Costas Spanos, the entire content of which is incorporated herein by reference). Comparing the logarithm of tan ($\Psi$) and cos ($\Delta$) rather than simply tan ($\Psi$) and cos ($\Delta$) has the advantage of being less sensitive to noise.

3. Obtaining Measured-Diffraction Signals from the Periodic Grating

In the present exemplary embodiment, prior to generating library 185, a measured-diffraction signal is obtained from at least one sample periodic grating 145. However, multiple measured-diffraction signals are preferably obtained from multiple sites on wafer 140. Additionally, multiple measured-diffraction signals can be obtained from multiple sites on multiple wafers 140. As will be described below, these measured-diffraction signals can be used in generating library 185.

4. Determining the Number of Hypothetical Parameters to Use in Modeling the Profile of the Periodic Grating In the present exemplary embodiment, a set of hypothetical parameters is used to model the profile of periodic grating 145 (FIG. 1). More particularly, a set of hypothetical parameters is used to define a hypothetical profile, which can be used to characterize the actual profile of periodic grating 145 (FIG. 1). By varying the values of the hypothetical parameters, a set of hypothetical profiles can be generated.

Figure 8A:
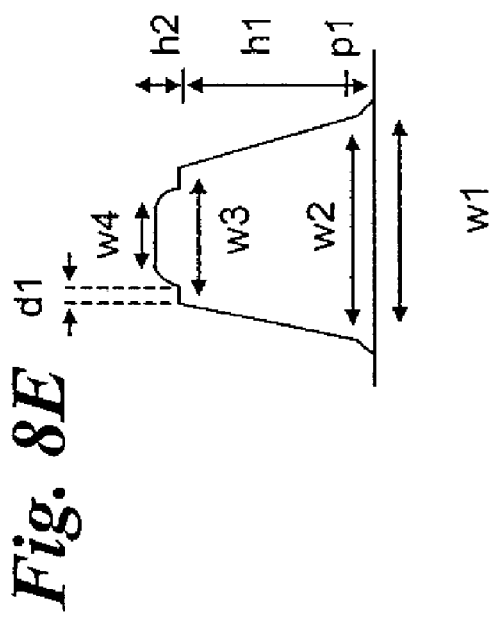
FIGS. 8A through 8E are cross-sections of various exemplary hypothetical profiles of periodic gratings.
Figure 8C:
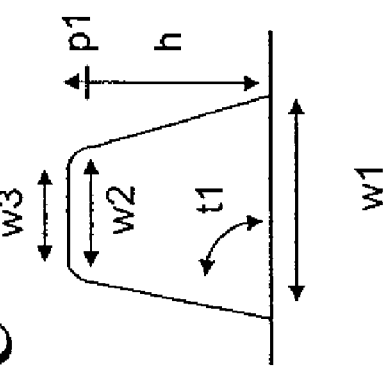

For example, with reference to FIG. 8A, two hypothetical parameters (i.e., h1 and w1) can be used to model a rectangular profile. As depicted in FIG. 5A, h1 defines the height of the hypothetical profile, and w1 defines the width of the hypothetical profile. By varying the values of h1 and w1, a set of rectangular hypothetical profiles can be generated.

Figure 8B:
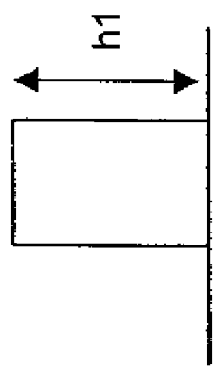

With reference now to FIG. 8B, three hypothetical parameters (i.e., h1, w1, and t1) can be used to model a trapezoidal profile. As depicted in FIG. 8B, t1 defines the angle between the bottom and side of the hypothetical profile. Again, by varying these hypothetical parameters, a set of hypothetical profiles can be generated.

With reference now to FIG. 5C, five hypothetical parameters (i.e., w1, w2, h, p1, and w3) can be used to model a trapezoidal profile with top rounding. As depicted in FIG. 5C, w1 defines the bottom width, w2 defines the top width of the trapezoidal profile, and w3 defines the width of the rounded top. Additionally, h defines the total height, p1 defines the height of the rounded top, and the ratio p1/h defines the percent of the height that is rounded. Again, by varying these hypothetical parameters, a set of hypothetical profiles can be generated.

Figure 8D:
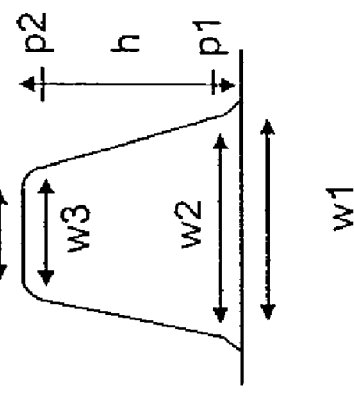

With reference now to FIG. 5D, seven hypothetical parameters (i.e., w1, w2, p1, h, p2, w3, and w4) can be used to model a trapezoidal profile with top rounding and bottom footing. As depicted in FIG. 8D, w1 defines the width of the bottom footing, w2 defines the bottom width of the trapezoidal profile, w3 defines the top width of the trapezoidal profile, and w4 defines the width of the rounded top. Additionally, h defines the total height, p1 defines the height of the bottom footing, and p2 defines the height of the rounded top. Thus, the ratio of p1/h defines the percent of the height that is the bottom footing, and the ratio of p2/h defines the percent of the height that is rounded. Again, by varying these hypothetical parameters, a set of hypothetical profiles can be generated.

Figure 8E:
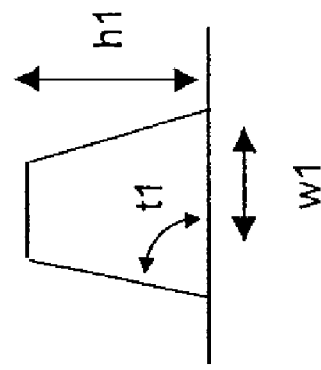

With reference now to FIG. 8E, eight hypothetical parameters (i.e., w1, w2, p1, h1, h2, w3, w4, and d1) can be used to model a trapezoidal profile with top rounding, bottom footing, and lateral offsets between two films. As depicted in FIG. 8E, w1 defines the width of the bottom footing, w2 defines the bottom width of the trapezoidal profile, w3 defines the top width of the trapezoidal profile, and w4 defines the width of the top film. Additionally, h1 defines the height of the first film, h2 defines the height of the 2nd film, p1 defines the height of the bottom footing, the ratio of p1/h1 defines the percent of the height of the first film that is the bottom footing, and d1 defines the offset between the first and second films. Again, by varying these hypothetical parameters, a set of hypothetical profiles can be generated.

In this manner, any number of hypothetical parameters can be used to generate hypothetical profiles having various shapes and features, such as undercutting, footing, t-topping, rounding, concave sidewalls, convex sidewalls, and the like. It should be understood that any profile shape could be approximated using combinations of stacked trapezoids. It should also be noted that although the present discussion focuses on periodic gratings of ridges, the distinction between ridges and troughs is somewhat artificial, and that the present application may be applied to any periodic profile.

As will be described in greater detail below, in the present embodiment, a simulated-diffraction signal can be generated for a hypothetical profile. The simulated-diffraction signal can then be compared with a measured-diffraction signal from periodic grating 145 (FIG. 1). If the two signals match, then the hypothetical profile is assumed to characterize the actual profile of periodic grating 145 (FIG. 1).

The accuracy of this match depends, in part, on the selection of the appropriate number of parameters to account for the complexity of the actual profile of periodic grating 145

(FIG. 1). More particularly, using too few parameters can result in coarse matches, and using too many parameters can unnecessarily consume time and computational capacity.

For example, assume that the actual profile of periodic grating 145 (FIG. 1) is substantially rectangular in shape. In this case, using two parameters, as depicted in FIG. 8A and described above, is sufficient to generate a set of hypothetical profiles to match the actual profile of periodic grating 145 (FIG. 1). However, the set of hypothetical profiles generated using three or more parameters can include hypothetical profiles generated using two parameters. More particularly, when t1 is 90 degrees, the hypothetical profiles generated using three parameters can include the set of rectangular hypothetical profiles generating using two parameters. However, since the actual profile of periodic grating 145 (FIG. 1) is rectangular, all of the hypothetical profiles generated using three parameters that are not rectangular (i.e., where t1 is not 90 degrees) are unnecessary. However, if the actual profile of periodic grating 145 (FIG. 1) is trapezoidal, then using two parameters would have resulted in a coarse match or no match.

As such, in the present exemplary embodiment, the measured-diffraction signals that were obtained prior to generating library 185 (FIG. 1) are used to determine the appropriate number of parameters to use in generating library 185 (FIG. 1). More particularly, in one configuration, the number of hypothetical parameters can be increased until the simulated-diffraction signal generated from the hypothetical profile defined by the hypothetical parameters matches the measured-diffraction signal within a desired tolerance. One advantage of increasing rather than decreasing the number of hypothetical parameters used is that it can be more time and computationally efficient since the larger sets of hypothetical profiles generated by the higher numbers of hypothetical parameters are not always needed.

Alternatively, in another configuration, the number of hypothetical parameters can be decreased until the simulated-diffraction signal generated from the hypothetical profile defined by the hypothetical parameters ceases to match the measured-diffraction signal within a desired tolerance. One advantage of decreasing rather than increasing the number of hypothetical parameters is that it can be more easily automated since the hypothetical profiles generated by lower numbers of hypothetical parameters are typically subsets of the hypothetical profiles generated by higher numbers of hypothetical parameters.

Additionally, in the present exemplary embodiment, a sensitivity analysis can be performed on the hypothetical parameters. By way of example, assume that a set of hypothetical parameters are used that include 3 width parameters (i.e., w1, w2, and w3). Assume that the second width, w2, is an insensitive width parameter. As such, when the second width, w2, is varied, the simulated-diffraction signals that are generated do not vary significantly. As such, using a set of hypothetical parameters with an insensitive parameter can result in a coarse or incorrect match between the hypothetical profile and the actual profile.

As such, in one configuration, after a match is determined between a simulated-diffraction signal and the measured-diffraction signal that was obtained prior to generating library 185 (FIG. 1), each hypothetical parameter in the set of hypothetical parameters used to generate the simulated-diffraction signal is perturbed and a new simulated-diffraction signal is generated. The greater the effect on the newly generated simulated-diffraction signal, the more sensitive the parameter.

Alternatively, in another configuration, after a match is determined between a simulated-diffraction signal and the measured-diffraction signal obtained prior to generating library 185 (FIG. 1), the number of hypothetical parameters used to generate the simulated-diffraction signal is increased or decreased by one. Assume that the number of hypothetical parameters was being increased to determine an appropriate number of hypothetical parameters to use in modeling periodic grating 145 (FIG. 1). In this case, the number of hypothetical parameters is increased by one and additional simulated-diffraction signals are generated. If a similar match is found between the measured-diffraction signal and one of these simulated-diffraction signals, then the additional hypothetical parameter is insensitive.

Assume now that the number of hypothetical parameters was being decreased to determine the appropriate number of parameters to use in modeling periodic grating 145 (FIG. 1). In this case, the number of hypothetical parameters is decreased by one and additional simulated-diffraction signals are generated. If a match is found between the measured-diffraction and one of these simulated-diffraction signals, then the hypothetical parameters that was removed is insensitive. The new adjusted parameterization will exclude all parameters deemed to be insensitive and include all parameters that were found to be sensitive.

Once the parameterization is completed, the critical dimension (CD) can then be defined based on any portion of the profile. Following are two examples of CD definitions based on the profile of FIG. 8E:

Definition 1: CD=w1
Definition 2: CD=w1/2+(4 w2+w3)/10

CD definitions can be user specific, and the above are typical examples that can be easily modified to suit different needs. Thus, it should be understood that there are a wide variety of CD definitions that will prove useful in various circumstances.

5. Adjusting the Range to Vary the Hypothetical Parameters in Generating a Set of Hypothetical Profiles As described above, a set of hypothetical profiles can be generated by varying the hypothetical parameters. As will be described in greater detail below, a simulated-diffraction signal can be generated for each of the hypothetical profile in this set. Thus, the range of simulated-diffraction signals available in library 185 (FIG. 1) is determined, in part, by the range within which the hypothetical parameters are varied.

As also describe above, an initial range over which the hypothetical parameters are to be varied can be obtained from users/customers. In some cases, however, this initial range is based on mere conjecture. Even when this initial range is based on empirical measurements, such as measurements of samples using AFM, X-SEM, and the like, inaccuracy in the measurement can produce poor results.

As such, in the present exemplary embodiment, the range over which the hypothetical parameters are to be varied is adjusted based on the measured-diffraction signal obtained prior to generating library 185 (FIG. 1). In brief, to determine the appropriateness of the range, multiple simulated-diffraction signals are generated until one matches one of the measured-diffraction signals. When a match is found, the hypothetical parameter values that were used to generate the matching simulated-diffraction signal are examined. More particularly, by determining where in the range these hypothetical parameter values fall, the appropriateness of the range can be determined, and the range can be adjusted as needed. For example, if these hypothetical parameters fall toward one end of the range, the range can be shifted and re-centered.

In the present exemplary embodiment, the range over which the hypothetical parameters are to be varied is adjusted before generating library 185 (FIG. 1). As will be described in greater detail below, the simulated-diffraction signals in library 185 (FIG. 1) are generated using the adjusted range of values for the hypothetical parameters. However, it should be understood that the range can be adjusted after generating library 185 (FIG. 1), then library 185 (FIG. 1) can be re-generated using the adjusted range.

Additionally, in the present exemplary embodiment, an optimization routine is used to generate matching simulated-diffraction signals. More particularly, a range of hypothetical parameters to be used in the optimization process is selected. Again, if the profile shape is known in advance, due to AFM or X-SEM measurements, a tighter range can be used. However, when the profile shape is not known in advance, a broader range can be used, which can increase the optimization time.

An error metric is selected to guide the optimization routine. In the present exemplary embodiment, the selected error metric is the sum-squared-error between the measured and simulated diffraction signals. While this metric can work well for applications where the error is identically and independently normally distributed (iind) and differences are relevant, it may not be a good metric for cases where the error is a function of the output value (and is hence not iind) and ratios are relevant. A sum-squared-difference-log-error can be a more appropriate error metric when the error is an exponential function of the output. Therefore, in the present embodiment, the sum-squared-error is used in comparisons of cos ($\Delta$), and the sum-squared-difference-log-error is used in comparisons of tan($\Psi$) where the ratio of the $0^{th}$ order TM reflectance to the zeroth order TE reflectance is given by tan($\Psi$)$e^{i\Delta}$.

After selecting an error metric, the optimization routine is run to find the values of the hypothetical parameters that produce a simulated-diffraction signal that minimizes the error metric between itself and the measured-diffraction signal. More particularly, in the present exemplary embodiment, a simulated annealing optimization procedure is used (see "Numerical Recipes," section 10.9, Press, Flannery, Teukolsky & Vetterling, Cambridge University Press, 1986, the entire content of which is incorporated herein by reference). Additionally, in the present exemplary embodiment, simulated-diffraction signals are produced by rigorous models (see University of California at Berkeley Doctoral Thesis of Xinhui Niu, "An Integrated System of Optical Metrology for Deep Sub-Micron Lithography," Apr. 20, 1999, the entire content of which is incorporated herein by reference).

In the present exemplary embodiment, if the simulated-diffraction signal matches the measured-diffraction signal to within a standard chi-squared goodness-of-fit definition (see Applied Statistics by J. Neter, W. Wasserman, G, Whitmore, Publishers. Allyn and Bacon, $2^{nd}$ Ed. 1982, the entire content of which is incorporated herein by reference), then the optimization is considered successful. The values of all of the hypothetical parameters are then examined and the CD is calculated.

This process is repeated to find matching simulated-diffraction signals for all of the measured-diffraction signals. The appropriateness of the range of the hypothetical parameters can then be determined by examining where the values of the hypothetical parameters of the matching simulated-diffraction signals lie in the range. For example, if they group near one end of the range, then the range can be shifted and re-centered. If they lie at the limits of the range, then the range can be broadened.

If the optimization process is unable to find a matching simulated-diffraction signal for a measured-diffraction signal, then either the range or the number of hypothetical parameters need to be altered. More particularly, the values of the hypothetical parameters are examined, and if they lie close to the limit of a range, then this is an indication that that range should be altered. For example, the range can be doubled or altered by any desirable or appropriate amount. If the values of the hypothetical parameters do not lie close to the limits of a range, then this typically is an indication that the number and/or type of hypothetical parameters being used to characterize the profile shape needs to be altered. In either case, after the range or the number of hypothetical parameters is altered, the optimization process is carried out again.

6. Determining the Number of Layers to Use in Dividing Up a Hypothetical Profile to Generate a Simulated-Diffraction Signal for the Hypothetical Profile As described above, a set of hypothetical parameters defines a hypothetical profile. A simulated-diffraction signal is then generated for each hypothetical profile. More particularly, in the present exemplary embodiment, the process of generating simulated-diffraction signals for a hypothetical profile includes partitioning the hypothetical profile into a set of stacked rectangles that closely approximates the shape of the hypothetical profile. From the set of stacked rectangles for a given hypothetical profile, the corresponding simulated-diffraction signals are generated (see University of California at Berkeley Doctoral Thesis of Xinhui Niu, "An Integrated System of Optical Metrology for Deep Sub-Micron Lithography," Apr. 20, 1999, the entire content of which is incorporated herein by reference; and U.S. patent application Ser. No. 09/764,780, entitled CACHING OF INTRA-LAYER CALCULATIONS FOR RAPID RIGOROUS COUPLED-WAVE ANALYSIS, filed on Jan. 17, 2001, the entire content of which is incorporated herein by reference).

Therefore, the quality of the library depends, in part, on how well the selected sets of stacked rectangles approximate the hypothetical profiles. Furthermore, since a typical library 185 (FIG. 1) can include hundreds of thousands of theoretical profiles, it is advantageous to rapidly automate the process of selecting a set of stacked rectangles for a hypothetical profile.

It should be noted that deciding on a fixed number of rectangles for a profile without consideration of the profile shape, and then representing the profile using the fixed number of rectangles of equal height, is not a rapid or efficient method. This is because the optimal number of rectangles that approximates one profile can be different from the optimal number of rectangles that approximate another profile. Also, the heights of the stacked rectangles that approximate a given profile need not be the same. Thus, in order to provide a good approximation, the number of rectangles, k, and the height of the rectangles are preferably determined for each profile.

However, the library generation time is a linear function of the number of rectangles, k. Consequently, increasing k in order to improve the library quality results in an increase in the amount of time required to generate a library 185 (FIG. 1). Therefore, it is advantageous to closely approximate each profile with a minimum number of rectangles by allowing rectangles to have variable heights.

Thus, in one exemplary embodiment, a process is provided to determine the number k of rectangles of varying heights that better approximate the shape of a profile. More particularly, this problem is transformed into a combinatorial optimization problem called a "set-cover" problem. Heuristics can then be used to solve the "set-cover" problem.

In brief, a set-cover problem involves a base set B of elements, and a collection C of sets C1, C2, . . . , Cn, where each Ci is a proper subset of B, and the sets C1, C2, . . . , Cn may share elements. Additionally, each set Ci has weight Wi associated with it. The task of a set-cover problem is to cover all the elements in B with sets Ci such that their total cost, $\Sigma_i Wi$, is minimized.

Returning to the present application of transforming the problem of rectangularization into a "set-cover" problem, let P denote a given profile. For ease of presentation, the profile P will be considered to be symmetric along the y-axis, so it is possible to consider only one side of the profile P. In the following description, the left half of the profile P is considered. Points on the profile are selected at regular intervals $\Delta y$ along y-axis, where $\Delta y$ is much smaller than the height of the profile. This selection allows the continuous curve to be approximated with discrete points denoted by p1, p2, . . . , pn. In other words, the points p1, 2, . . . , pn correspond to the coordinates (x1, 0), (x2, $\Delta y$), . . . (xn, (n−1) $\Delta y$), respectively. These points p1, p2, . . . , pn form the base set B and the sets in C correspond to the rectangles that can be generated by these points.

Figure 5:
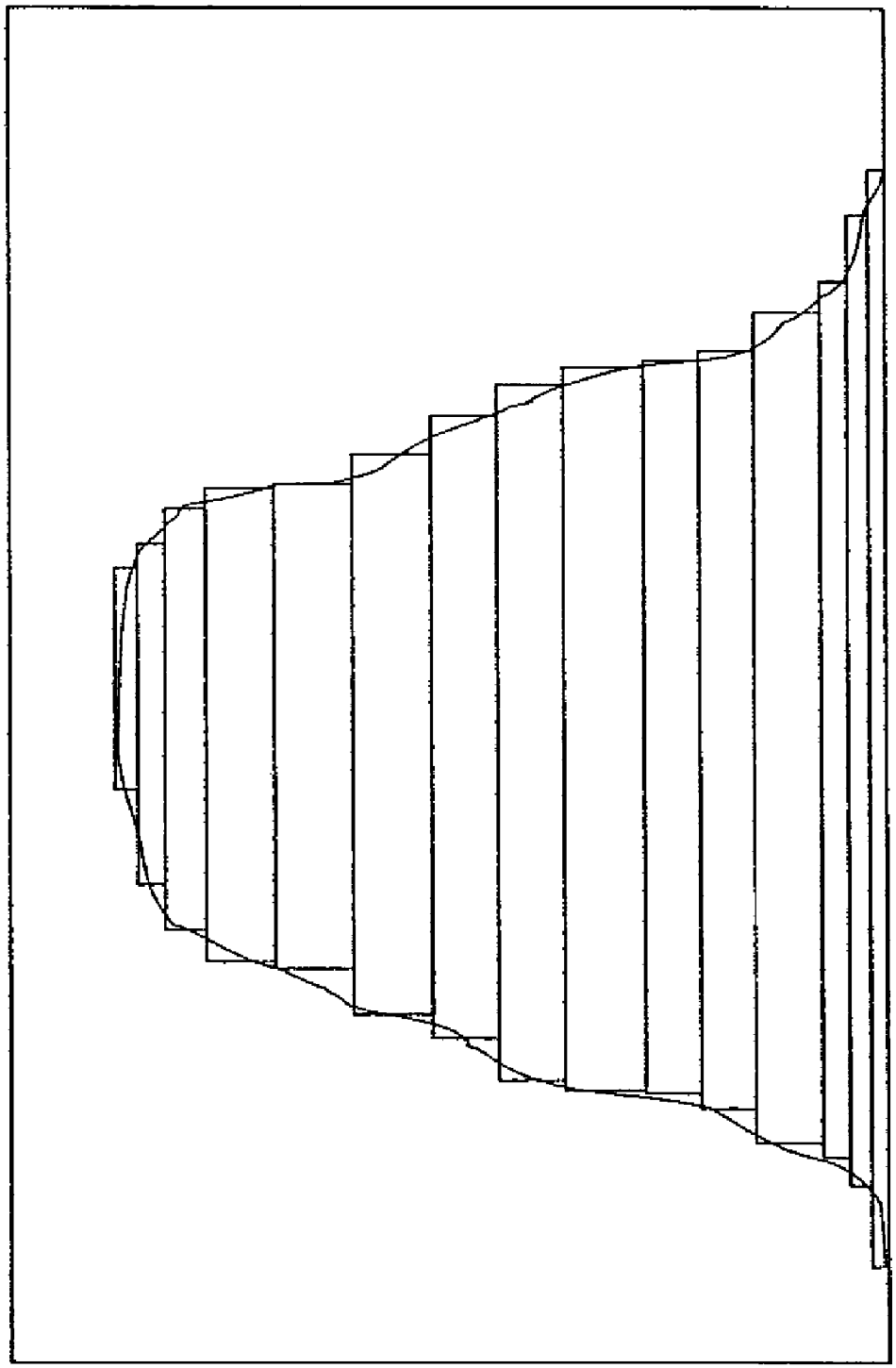
FIG. 5 is a graphical depiction of an exemplary hypothetical profile of a periodic grating.
Figure 6:
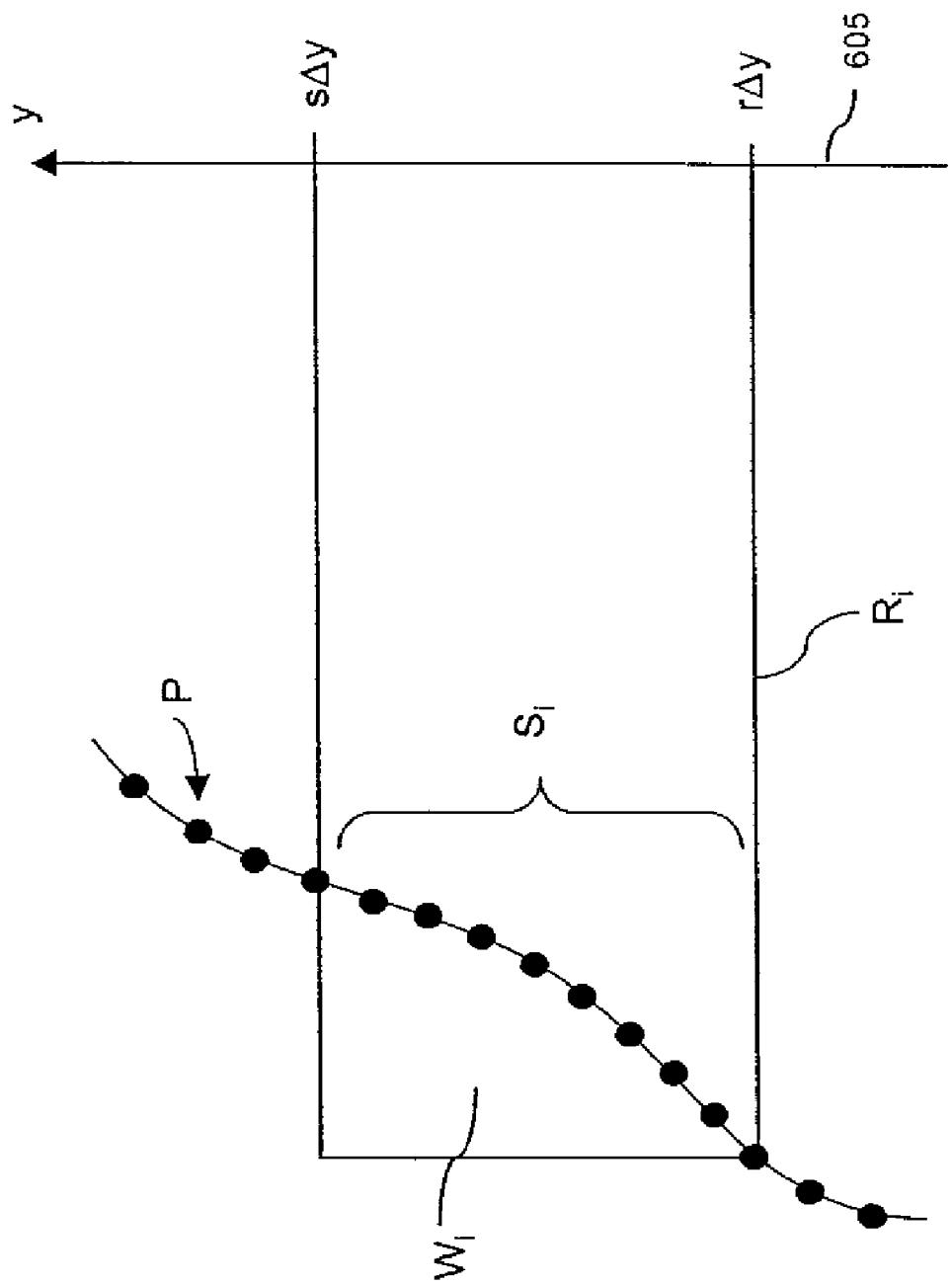
FIG. 6 is a graph depicting the mapping of a rectangularization problem as a set-cover problem.
Figure 7:
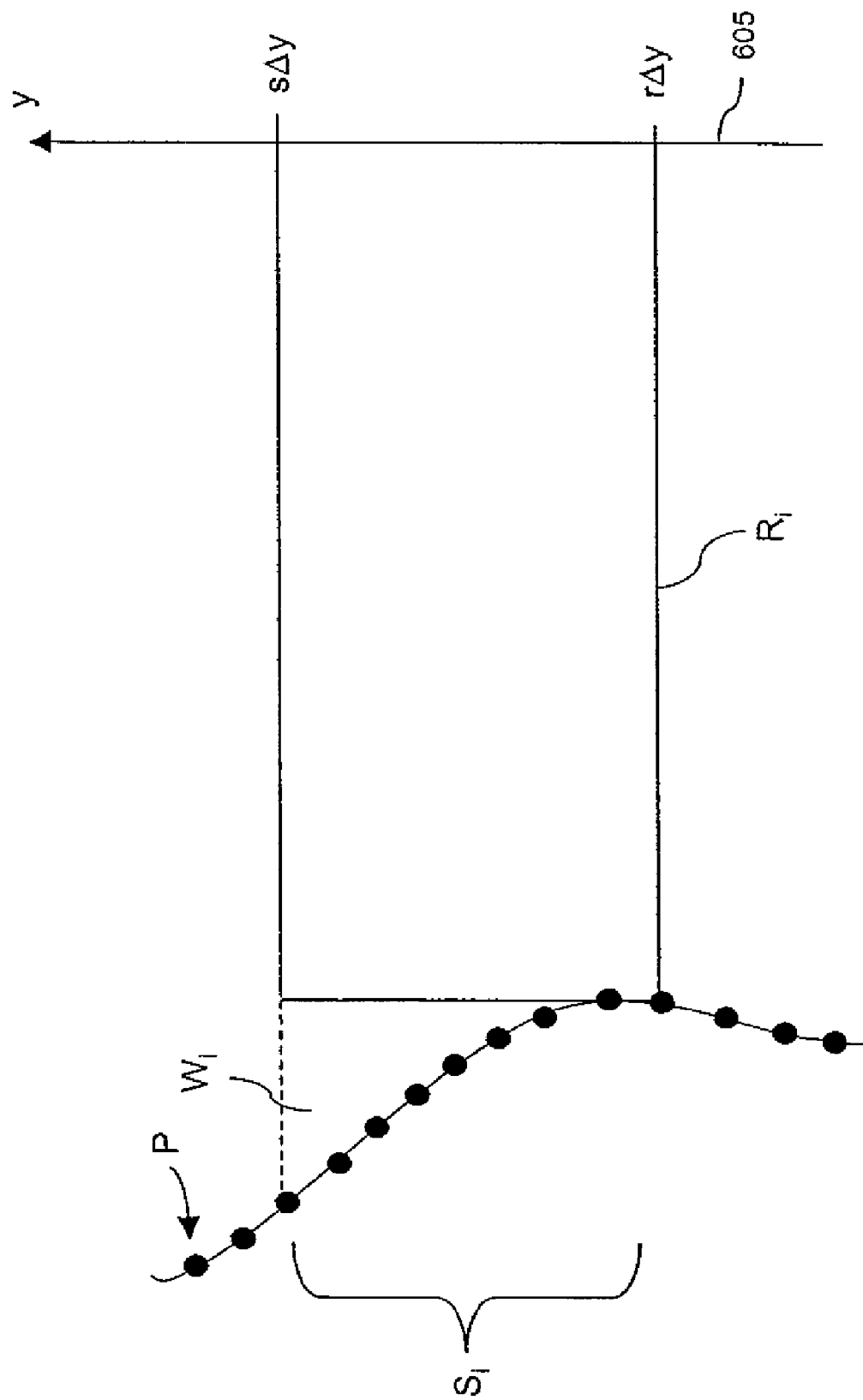
FIG. 7 is another graph depicting the mapping of another rectangularization problem as a set-cover problem.

As shown in the exemplary rectangularization of FIG. 5, each rectangle has its bottom left corner at point pi from B, and its top left corner has the same x-coordinate as its bottom left coordinate. Additionally, the y-coordinate of its top left corner is some value j$\Delta y$, where j$\geq$i. Thus, there are (n*(n−1))/2 different rectangles that can be formed by selecting two heights i$\Delta y$ and j$\Delta y$ along the profile—these rectangles have all possible heights from $\Delta y$ to n$\Delta y$, and all possible positions in the profile P as long as the top and bottom of the rectangle lies within (or at the top or bottom edges of) the profile P. These rectangles are denoted by R1, R2, . . . , Rm, where m=(n*(n−1))/2. With reference to FIG. 6, the left-hand edge of rectangle Ri, which extends vertically from r$\Delta y$ to s$\Delta y$, where r and s are integers such that 0$\leq$r<s$\leq$n, approximates a subregion of P denoted by Si, and the set Ci includes all the points of the profile P that lie within Si, i.e., all points on the profile P with y coordinates between r$\Delta y$ and s$\Delta y$.

Thus, a set system C that has its sets C1, C2, . . . , Cm is established. Weights are then assigned to the sets Ci. Since the objective of a set-cover problem is to minimize the total cost of the cover, the weights Wi are assigned to reflect that goal, i.e., to approximate the profile shape by quantifying the quality of approximation. Therefore, as shown in FIG. 6, the weight Wi assigned to rectangle RI is the difference in area between the area of rectangle Ri and the area between section Si of the profile P and the y axis 605. As shown in FIG. y, where section Si lies outside of rectangle Ri, the weight Wi is considered to be a positive number. The larger the weight Wi/|Ci|, where |Ci| denotes the cardinality of set Ci, the worse the rectangle Ri is as an approximation of the profile P.

Thus far the mapping between a set-cover problem and the rectangularization of the profile has been presented. The next step is to solve the set-cover problem. It has been shown that solving a set-cover problem is computationally difficult since the running time of the best known exact-solution algorithm is an exponential function of the input size. However, there are a number of efficient heuristics that can generate near-optimal solutions.

For example, a heuristic called a "greedy" heuristic can be used. At every step, this heuristic selects the set Ci whose value of Wi/|Ci| is the least. It then adds Ci to the solution set Z and deletes all the elements in Ci for the base set B, and deletes any other sets Cj that share any elements with Ci. Additionally, any empty set in C is removed from it. Thus, at every step, the number of elements in the base set B decreases. This process is repeated until the base set B is empty. At this point, the solution set Z consists of sets that cover all the profile points pi. The sets in the solution Z can be transformed back into the rectangles which approximate the profile P. It should be noted that the value of |Ci| at a given stage is the number of elements that it contains in that stage—not the number of elements that it originally started with. Since the selection of sets Ci depends on the value Wi/|Ci|, the rectangles that are obtain can have different sizes. A detailed description on the basic algorithm of this heuristic can be found in an article entitled "Approximation algorithms for clustering to minimize the sum of diameters," by Srinivas Doddi, Madhav Marathe, S. S. Ravi, David Taylor, and Peter Widmayer, Scandinavian workshop on algorithm theory (SWAT) 2000, Norway, the entire content of which is incorporated herein by reference.

Although the above method returns a set of rectangles that approximate a given profile, the number of rectangles might be very large. In the above mentioned article, Doddi, et. al found that by uniformly increasing the weights of each set by $\Delta w$ and rerunning the above method, the number of rectangles will be reduced. By repeating this process for increasing values of $\Delta w$, it is possible to achieve a target number of rectangles.

Although rectangles have been described as being used to represent profile shapes, it should be noted that any other geometric shape, including trapezoids, can be used. A process for automatically approximating a profile with trapezoids may, for instance, be applied to the step of adjusting the range to vary the parameters in generating a set of simulated-diffraction signals.

7. Determining, the Number of Harmonic Orders to Use in Generating the Set of Simulated-Diffraction Signals As described above, in the present exemplary embodiment, simulated-diffraction signals can be generated using a rigorous coupled wave analysis (RCWA). For a more detailed description of RCWA, see T. K. Gaylord, M. G. Moharam, "Analysis and Applications of Optical Diffraction by Gratings", Proceedings of the IEEE, vol. 73, no. 5, May 1985, the entire content of which is incorporated herein by reference.

Prior to performing an RCWA calculation, the number of harmonic orders to use is selected. In the present exemplary embodiment, an Order Convergence Test is performed to determine the number of harmonic orders to use in the RCWA calculation. More particularly, simulated-diffraction signals are generated using RCWA calculations with the number of harmonic orders incremented from 1 to 40 (or higher if desired). When the change in the simulated-diffraction signal for a pair of consecutive order values is less at every wavelength than the minimum absolute change in the signal that can be detected by the optical instrumentation detector (e.g., detector 170 in FIG. 1), the lesser of the pair of consecutive orders is taken to be the optimum number of harmonic orders.

When multiple profile shapes are determined in characterizing periodic grating 145 (FIG. 1), an Order Convergence Test can be performed for each of these profile shapes. In this manner, the maximum number of harmonic orders obtained from performing the Order Convergence Test is then used in generating library 185 (FIG. 1).

8. Determining a Resolution to Use in Generating the Set of Simulated-Diffraction Signals As described earlier, the value of hypothetical parameters are varied within a range to generate a set of hypothetical profiles. Simulated-diffraction signals are then generated for the set of hypothetical profiles. Each simulated-diffraction signal is paired with a hypothetical profile, then the pairings are stored in library 185 (FIG. 1). The increment at which the hypothetical parameters are varied determines the library resolution of library 185 (FIG. 1). As such, the smaller the increment, the finer the resolution, and the larger the size of the library.

Thus, the resolution of hypothetical parameters used in generating library 185 (FIG. 1) is determined to provide a compromise between (1) the minimization of the size of the library by using large library resolutions, and (2) providing accurate matches between signals and profiles by using small library resolutions. More particularly, in the present exemplary embodiment, an abbreviated library is generated using a portion of the range used to generate the full library. Using the abbreviated library, the lowest resolution is determined for the hypothetical parameters that do not have specified resolutions that still provide accurate matches for the critical parameters.

By way of example, assume that three hypothetical parameters (top CD, middle CD, and bottom CD) are used to characterize a profile. Assume that the range for the top CD, middle CD, and bottom CD are 60 to 65 nanometers, 200 to 210 nanometers, and 120 to 130 nanometers, respectively. Also assume that the critical parameter is the bottom CD and the specified resolution for the bottom CD is 0.1 nanometer, and no particular resolution is specified for the top and middle CDs.

In the present exemplary embodiment, an abbreviated library is generated using a portion of the range specified for the hypothetical parameters. In this example, an abbreviated library of simulated-diffraction signals is generating for top CD between 60 and 61, middle CD between 200 and 201, and bottom CD between 120 and 121.

Initially, the abbreviated library is generated at the highest specified resolution. In this example, simulated-diffraction signals are generated for the top CD, middle CD, and bottom CD as they are incremented by 0.1 nanometers between their respective ranges. For example, simulated-diffraction signals are generated for a top CD of 60, 60.1, 60.2, . . . , 60.9, and 61. Simulated-diffraction signals are generated for middle CD of 200, 200.1, 200.2, . . . , 200.9, and 201. Simulated-diffraction signals are generated for bottom CD of 120, 120.1, 120.2, . . . , 120.9, and 121.

The resolution of the non-critical parameters is then incrementally reduced in the abbreviated library until an attempted match for the critical parameter fails. In this example, the simulated-diffraction signal corresponding to the set of hypothetical parameters with top CD of 60.1, middle CD of 200, and bottom CD of 120 is removed from the abbreviated library. An attempt is then made to match the removed simulated-diffraction signal with remaining simulated-diffraction signals in the abbreviated library. If a match is made with a simulated-diffraction signal having the same critical parameter as the removed simulated-diffraction signal (i.e., a bottom CD of 120), then the resolution for the top CD can be further reduced. In this manner, each of the non-critical parameters are tested to determine the minimum resolution that can be used. This study is performed for all the non-critical parameters simultaneously in order to take into account the parameter interaction effects.

In the following description, a more thorough description is provided of a process for determining the resolution $\Delta p_i$ of hypothetical parameters $p_i$ used in generating library 185 (FIG. 1) is determined to provide a compromise between (1) the minimization of the size of the library by using large library resolutions $\Delta p_i$, and (2) providing accurate matches between signals and profiles by using small library resolutions $\Delta p_i$.

Figure 9:
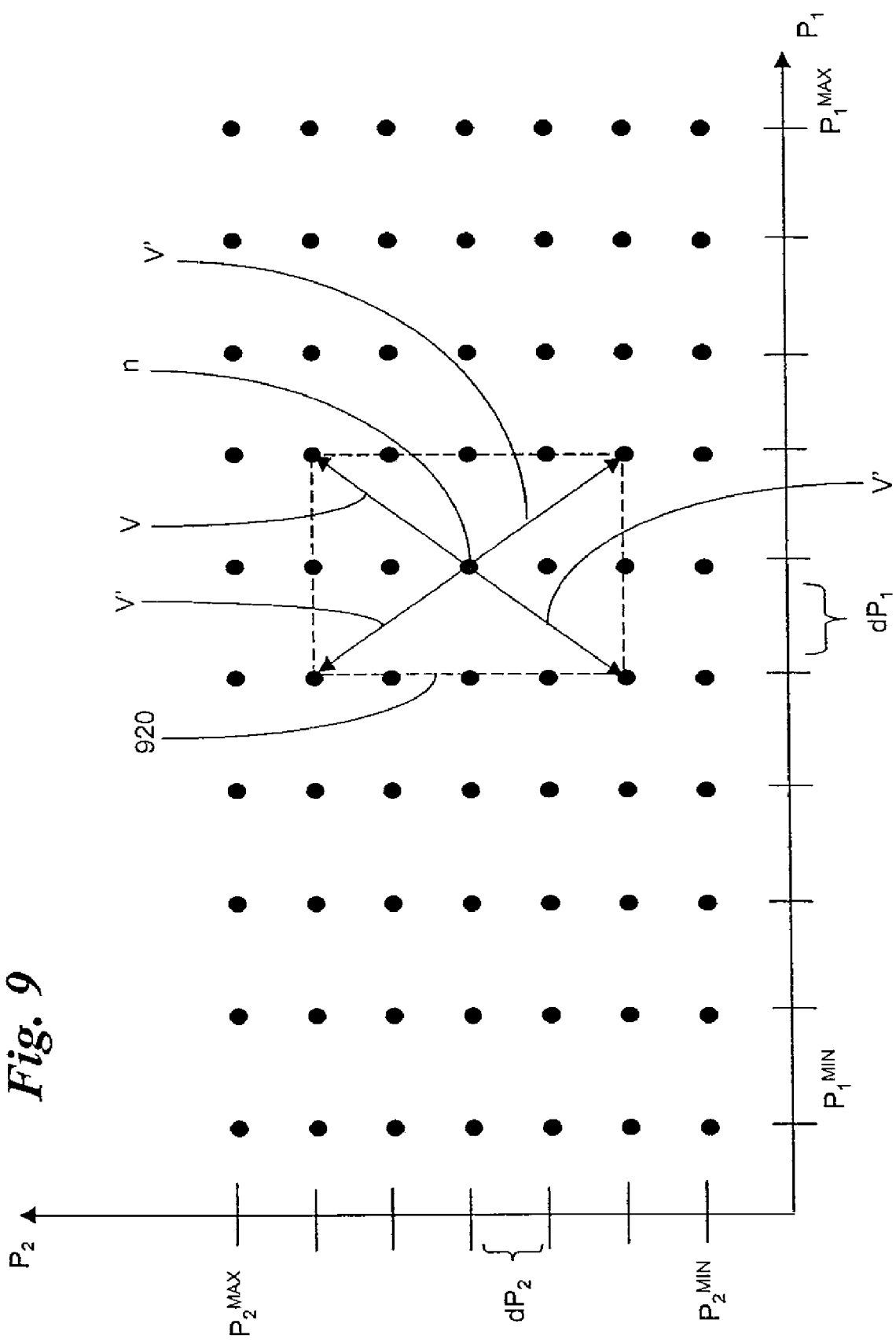
FIG. 9 is a graph of two parameters.

The parameters $p_i$ which are used to characterize various profiles P were described in detail above. In the following description, the general case of m parameters $p_1, p_2, \ldots, p_m$ will be presented, and the special case of m=2 will be depicted in FIG. 9 and presented in text enclosed in curly brackets "{ }". {For concreteness, consider the first parameter $p_1$ to be the width w1 of a rectangular profile, and the second parameter $p_2$ to be the height h1 of a rectangular profile.} Therefore, any profile P may be represented by a point in an m-dimensional space. {Therefore, as shown in FIG. 9, any profile P may be represented by a point in a two-dimensional space.} The range of profiles P to be used in library 185 (FIG. 1) may be specified by setting minimum and maximum values of each parameter $p_i^{(min)}$ and $p_i^{(max)}$.

Typically, the particular resolution of interest in semiconductor fabrication, i.e., the target resolution R, is the resolution of the critical dimension. In general, the resolution of the critical dimension is some function of the resolution $\Delta p_i$ of multiple parameters $p_i$. {In the two-dimensional case, the resolution of the critical dimension happens to be the resolution $\Delta p_1$ of the first parameter $p=w_1$. But to make the two-dimensional discussion correspond to the general case, the critical dimension will be assumed to be a function of the resolution $\Delta p_i$ of multiple parameters $p_i$.}

Typically only a single target resolution R is considered. However, in the present embodiment, multiple target resolutions $R_i$ can be considered, and the accuracy of the mappings between profiles and signals allows the resolution $\Delta p_i$ of multiple profile shape parameters $p_i$ to be determined.

A grating of a particular profile P produces a complex-valued diffraction signal $S(P, \lambda)$, which is plotted as a function of wavelength $\lambda$. The magnitude of the signal $S(P, \lambda)$ is the intensity, and the phase of the signal $S(P, \lambda)$ is equal to the tangent of the ratio of two, perpendicular planar polarizations of the electric field vector. A diffraction signal may, of course, be digitized, and the sequence of digital values may be formed into a vector, albeit a vector having a large number of entries if the signal is to be accurately represented. Therefore, each signal $S(P, \lambda)$ corresponds to a point in a high-dimensional signal space, and points in the high-dimensional space which are near each other correspond to diffraction signals which are similar. For ease of depiction in the present discussion, in FIG. 10 a signal space with a dimensionality of two, $s_1$ and $s_2$, is shown. The two-dimensional depiction of FIG. 10 may be considered to be a projection of the high-dimensionality signal space onto two dimensions, or a two-dimensional slice of the signal space.

In the present embodiment, the determination of the library resolutions $\Delta p_i$ of the parameters $p_i$ begins by choosing a nominal profile $p^{(n)}$, and generating its corresponding signal $S(P^{(n)})$. Then a set of profiles P near the nominal profile $P^{(n)}$ is generated. This may be done by choosing a regularly-spaced array of points in the profile space around the nominal n, an irregularly-spaced array of points in the profile space around the nominal n, or a random scattering of points in the profile space around the nominal n. For ease of discussion and depiction, a regularly-spaced array of points around the nominal n will be considered {and depicted in FIG. 9}, so parameter increment values $\delta p_i$ are chosen for each parameters $p_i$. Therefore, profiles located at $n + \Sigma_i a_i \delta p_i$, and the corresponding diffraction signals $$S(n+\Sigma_i a_i \delta p_i)$$

are generated, where $a_i$ takes integer values ($\ldots, -2, -1, 0, 1, 2, 3, \ldots$) and the sum runs from i=1 to i=m, and n is the vector corresponding to the nominal profile $P^{(n)}$. {Therefore, as shown in FIG. 9, profiles located at $$n+a_1 \delta p_1 + a_2 \delta p_2,$$

and the corresponding diffraction signals, $$S(n+a_1 \delta p_1 + a_2 \delta p_2),$$

are generated, where $a_1$ and $a_2$ take integer values ($\ldots, -2, -1, 0, 1, 2, 3, \ldots$).} (For ease of presentation, a profile P and its corresponding vector in the profile space will be used synonymously.) The parameter increment values $\delta p_i$ are chosen to be small relative to the expected values of the library resolutions $\Delta p_i$, i.e., $$\delta p_i << \Delta p_i.$$

Figure 10:
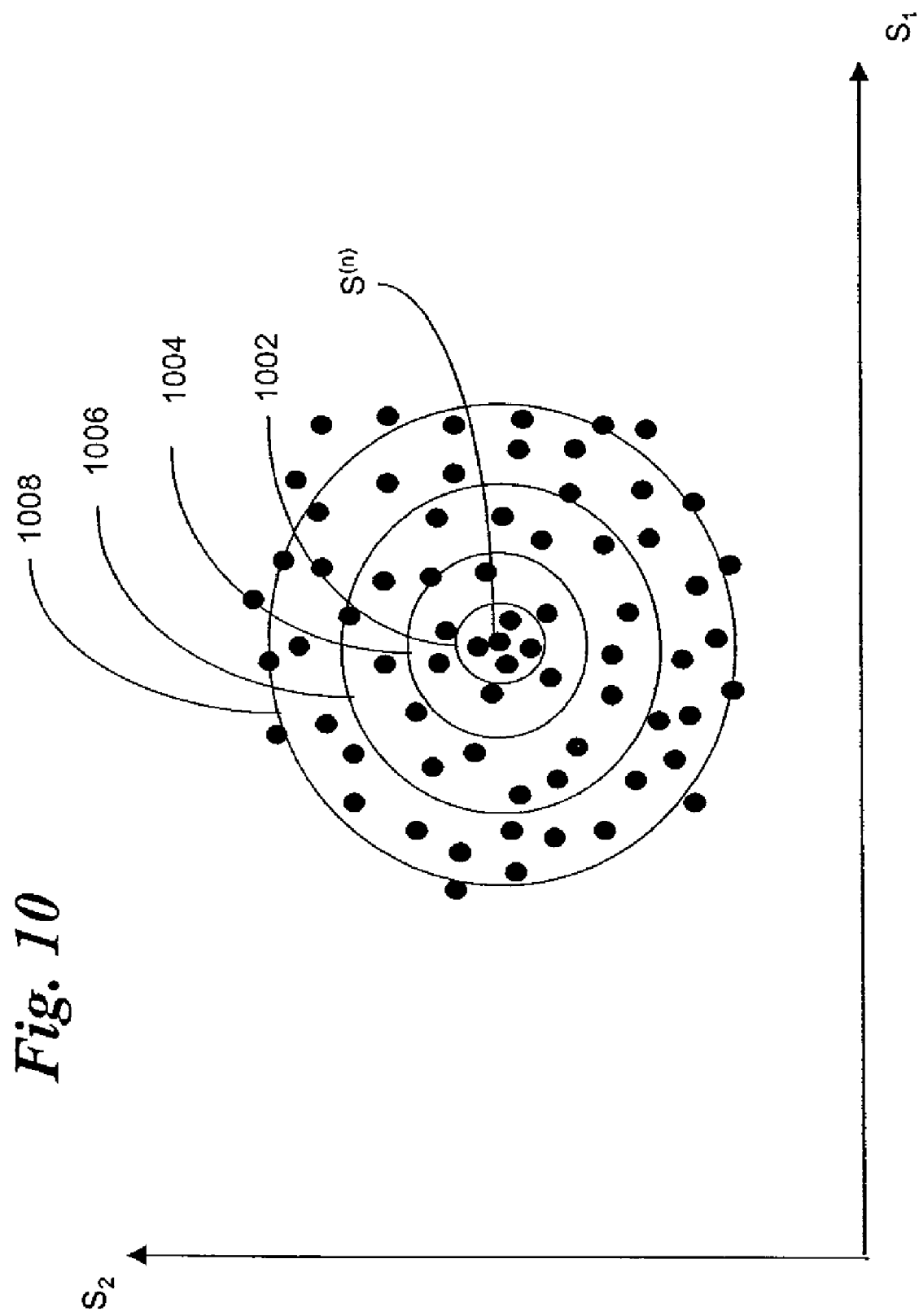
FIG. 10 is a signal space.

{In the example shown in FIG. 9, the parameter increment values $\delta p_1$ and $\delta p_2$ are chosen to be one-eighth and one-sixth the size of the ranges $(p_1^{(max)} - p_1^{(min)})$ and $(p_2^{(max)} - p_2^{(min)})$, respectively, of parameter values used in determining the resolutions of the parameters.} In practice, the parameter increment values $\delta p_i$ are chosen to be orders of magnitude smaller than the sizes of the ranges $(p_1^{(max)} - p_1^{(min)})$ and resolutions $\Delta p_i$ of parameter values. While the profiles P may be selected to correspond to points on a grid, generally the corresponding diffraction signals S, which are depicted as dots in FIG. 10, are not located at regularly spaced intervals.

The next step in determining the resolutions $\Delta p_i$ of the parameters $p_i$, is to order the signals $S(n+a_1 \delta p_1 + a_2 \delta p_2)$ by increasing distance from the signal S(n) of the nominal profile $P^{(n)}$, which will hereafter be referred to as the nominal signal S(n) or $S^{(n)}$. In the present embodiment, the distance between a first signal $S^{(1)}$ and a second signal $S^{(2)}$ is measured using a sum-squared-difference-log error measure $\Phi$, i.e., $$\Phi(S^{(1)}, S^{(2)}) = \Sigma_\lambda [\log S^{(1)}(\lambda) - \log S^{(2)}(\lambda)]^2,$$

where the sum is taken over uniformly-spaced wavelengths $\lambda$. As shown in FIG. 10, this is graphically represented by drawing a series of closely spaced hyperspheres, which are represented in FIG. 10 as circles 1002, 1004, 1006, and 1008, centered around the nominal signal S(n), and ordering the signals $S(n+\Sigma_i a_i \delta p_i)$ {$S(n+a_1 \delta p_1 + a_2 \delta p_2)$} according to the largest hypersphere 1002, 1004, 1006, and 1008 which encloses each signal $S(n+\Sigma_i a_i \delta p_i)$ {$S(n+a_1 \delta p_1 + a_2 \delta p_2)$}. The smallest hypersphere 1002 corresponds to the resolution $\in$ of the instrumentation, i.e., all signals S within the smallest hypersphere 1002 satisfy $$S^{(n)}(\lambda) - S(\lambda) \leq \in,$$

at all wavelengths $\lambda$. In the exemplary case of FIG. 10, four signals are shown to be within circle 1002.

According to the next step of the present invention, the signals $S(n+\Sigma_i a_i \delta p_i)\{S(n+a_1 \delta p_1 + a_2 \delta p_2)\}$ are tested in order of increasing distance $\Phi$ from the nominal signal $S^{(n)}$ to determine which is the signal $S(n+\Sigma_i a_i \delta p_i)\{S(n+a_1 \delta p_1 + a_2 \delta p_2)\}$ closest to the nominal signal $S^{(n)}$ which has a profile $(n+\Sigma_i a_i \delta p_i)\{S(n+a_1 \delta p_1 + a_2 \delta p_2\}$ which differs from the nominal profile $P^{(n)}$ by the target resolution R. In the case of multiple target resolutions R, the signals $S(n+\Sigma_i a_i \delta p_i)\{S(n+a_1 \delta p_1 + a_2 \delta p_2)\}$ are tested in order of increasing distance $\Phi$ from the nominal signal $S^{(n)}$ to determine which is the signal $S(n+\Sigma_i a_i \delta p_i)\{S(n+a_1 \delta p_1 + a_2 \delta p_2)\}$ closest to the nominal signal $S^{(n)}$ which has a profile $(n+\Sigma_i a_i \delta p_i)\{n+a_1 \delta p_1 + a_2 \delta p_2\}$ which differs from the nominal profile $P^{(n)}$ by one of the target resolutions $R_i$. That particular signal is termed the border signal $S^{(B)}$, and the smallest hypersphere 1002, 1004, 1006, and 1008 which encloses the border signal $S^{(B)}$ is termed the border hypersphere B. For those signals S which fall outside the border hypersphere B, the corresponding profiles P are discarded from consideration in the process of determining the library resolutions $\Delta p_i$.

Then, for each signal S which lies within the border hypersphere B, a displacement vector V for its relation to the nominal profile vector n is determined. In particular, the displacement vector V between a profile $P^{(a)}$ described by the vector $(p_1^a, p_2^a, \ldots, p_m^a)$ and the nominal vector $n = (p_1^n, p_2^n, \ldots, p_m^n)$ is given by $$V = (p_1^a - p_1^n, p_2^a - p_2^n, \ldots, p_m^a - p_m^n),$$

{or in the two-dimensional case depicted in FIG. 9, $$V = (p_1^a - p_1^n, p_2^a - p_2^n).$$

The exemplary displacement vector V shown in FIG. 9 is V=(1, 2).} The set of equivalent displacement vectors V' is defined as $$V' = (\pm|p_1^a - p_1^n|, \pm|p_2^a - p_2^n|, \ldots, \pm|p_m^a - p_m^n|),$$

{or in the two-dimensional case depicted in FIG. 9, $$V' = (\pm|p_1^a - p_1^n|, \pm|p_2^a - p_2^n|),\}$$

i.e., the set of equivalent displacement vectors V', which includes the original displacement vector V, defines the $2^m$ {four} corners of an m-dimensional hyperrectangle {a two-dimensional rectangle 920 depicted in FIG. 9}.

Then, for each signal S(V) which lies within the border hypersphere B, it is determined whether all the equivalent displacement vectors V' correspond to signals S(V') which also lie within the hypersphere B. If one or more signals S(V') do not lie within the hypersphere B, the profiles corresponding to the entire set of the equivalent displacement vectors V' are discarded from consideration in the process of determining the library resolutions $\Delta p_i$. In other words, what remains under consideration in determining the library resolutions $\Delta p_i$ are those m-dimensional hyperrectangles {two-dimensional rectangles} in profile space for which all the corresponding signals S lie inside the border hypersphere B. It is these m-dimensional hyperrectangles {two-dimensional rectangles} which are under consideration as the library resolutions $\Delta p_i$.

For each of the m-dimensional hyperrectangles {two-dimensional rectangles} in profile space for which all the corresponding signals S lie inside the border hypersphere B, the number N of m-dimensional hyperrectangles {two-dimensional rectangles} required to fill the profile space is simulated. For a $p_1^* \times p_2^* \times \ldots \times p_m^*$ hyperrectangle, the count number N is the number of such $p_1^* \times p_2^* \times \ldots \times p_m^*$ hyperrectangles which fit into a hyperrectangular space defined by the bounds $p_i^{(min)} < p_i < p_i^{(max)}$. The count number N is given by $$N = \max[(p_1^{(max)} - p_1^{(min)})/p_1^*, (p_2^{(max)} - p_2^{(min)})/p_2^*, \ldots],$$

where the square brackets in the above equation indicate that each fractional value within is rounded up to the nearest integer. {For instance, for the 2 $\delta p_1 \times 4$ $\delta p_2$ rectangle 620 defined by the equivalent vectors V' shown in FIG. 9, since the rectangular profile space has a width of $(p_1^{(max)}-p_1^{(min)})=9\delta p_1$ and a height of $(p_2^{(max)}-p_2^{(min)})=6\delta p_2$, the count number N is five.}

Finally, the resolutions $\Delta p_i$ which are used for the library are equal to the dimensions of the m-dimensional hyperrectangle defined by the set of equivalent vectors V' which (i) has the smallest count N, and for which (ii) all the corresponding signals S(V') lie inside the border hypersphere B.

9. Generating the Set of Simulated-Diffraction Signals Based on the Adjusted Range Parameterization, and/or Resolution In the present exemplary embodiment, library 185 (FIG. 1) is generated, wherein both the profile shape and the film geometry (thickness and width) parameters are varied using the adjusted parameterization, ranges and resolutions determined above. As such, the number of profiles generated in library 185 (FIG. 1) is a function of the profile shape parameterization and the ranges and resolutions of the parameters. Additionally, the library entries are a function of grating pitch, optical properties of films in the underlying and patterned layers, profile parameter ranges, profile parameter resolutions and profile shapes. It should be noted that library 185 (FIG. 1) can be generated by using only the adjusted ranges or only the adjusted resolution.

10. Comparing a Set of Measured-Diffraction Signals with the Simulated-Diffraction Signals in the Library In the present exemplary embodiment, after generating library 185 (FIG. 1), a set of measured-diffraction signals are compared with the simulated-diffraction signals in library 185 (FIG. 1), as a quality control. If the error between the best match found in library 185 (FIG. 1) and the measured-diffraction signal is better than a threshold goodness-of-fit limit, then the library generation process is considered successful. Alternatively, and more preferably, a quality control can be insured by comparing the width and height values obtained using another measurement technique, such as an X-SEM, CD-SEM, and the like.

Although exemplary embodiments have been described, various modifications can be made without departing from the spirit and/or scope of the present invention. Therefore, the present invention should not be construed as being limited to the specific forms shown in the drawings and described above.

We claim:

1. A method of generating simulated diffraction signals of a structure formed on a wafer, said method comprising:
    associating hypothetical parameters with a hypothetical profile of the structure to be examined;
    incrementally determining the number of harmonic orders to use in generating simulated diffraction signals;
    generating a simulated diffraction signal using the hypothetical profile and the determined number of harmonic orders; and
    storing the simulated diffraction signal.

2. The method of claim 1, wherein incrementally determining the number of harmonic orders includes running a convergence test.

3. The method of claim 2 further comprising:
    obtaining a measured diffraction signal of the structure;
    generating simulated diffraction signals using increasing number of orders;
    determining the change in the simulated diffraction signals with the increase in the number of orders used; and
    selecting the lower number of orders when the change in the simulated diffraction signals is less than the minimum change in the measured diffraction signal that can be obtained.

4. The method of claim 3, wherein the lower number of orders is selected when the change in the simulated diffractions for a pair of consecutive order values is less at every wavelength than the minimum change iii the measured diffraction signal that can be obtained.

5. The method of claim 1 wherein incrementally determining the number of harmonic orders comprises:
    obtaining a measured diffraction signal of the structure;
    generating simulated diffraction signals using increasing number of orders;
    determining the change in the simulated diffraction signals with the increase in the number of orders used; and
    selecting the lower number of orders when the change in the simulated diffraction signals for a pair of consecutive order values is less than the minimum change in the measured diffraction signal that can be obtained.

6. The method of claim 1 further comprising:
    dividing the hypothetical profile into a plurality of hypothetical layers; and
    determining the number of hypothetical layers to use in generating a set of simulated signals for the hypothetical profile.

7. The method of claim 6, wherein determining the number of hypothetical layers includes:
    mapping the determination of the number of hypothetical layers as a set-cover problem; and
    solving the set-cover problem.

8. The method of claim 1 further comprising:
    obtaining a measured diffraction signal of the structure;
    varying the hypothetical parameters within a range to generate a set of hypothetical profiles; and
    adjusting the range to vary the hypothetical parameters based on the measured signal.

9. The method of claim 8, wherein adjusting the range to vary the hypothetical parameters includes:
    generating a set of simulated diffraction signals from the set of hypothetical profiles;
    comparing the simulated diffraction signals of the set and the measured diffraction signal using an error metric; and
    shifting the range to vary the hypothetical parameters when a simulated diffraction signal of the set and the measured signal match and when the hypothetical parameters of the simulated diffraction signal lie near an upper or lower limit of the range.

10. The method of claim 1 further comprising:
    generating a set of simulated diffraction signals from a set of hypothetical profiles;
    determining a resolution for the set of simulated signals; and
    varying the hypothetical parameters used in generating the simulated signals at an increment corresponding to the determined resolution.

11. The method of claim 10, wherein the resolution for the parameters is determined based on a desired critical dimension of the periodic grating.

12. The method of claim 11, wherein determining the resolution for the parameters further comprises:
    generating a sub-set of simulated signals including:
        a first-simulated signal generated using a first set of hypothetical parameters, wherein the first set of hypothetical parameters includes:
            a first-hypothetical parameter associated with the desired critical dimension, and
            a second-hypothetical parameter not associated with the desired critical dimension, and a second-simulated signal generated using a second set of hypothetical parameters, wherein the second set of hypothetical parameters includes:
   a first-hypothetical parameter matching the first-hypothetical parameter of the first-simulated signal, and
   a second-hypothetical parameter not associated with the desired critical dimension and not matching the second-hypothetical parameter of the first-simulated signal;
removing the second-simulated signal from the sub-set of simulated signals;
comparing the second-simulated signal to the remaining simulated signals in the sub-set of simulated signals; and
reducing the resolution to use for the second-hypothetical parameter in generating the set of simulated signals if the comparison matches the second-simulated signal to the first-simulated signal.

13. The method of claim 1, wherein associating hypothetical parameters with a hypothetical profile further comprises:
   obtaining a measured diffraction signal of the structure; and
   determining the number of hypothetical parameters to associate with the hypothetical profile based on the measured signal.

14. The method of claim 13, wherein determining the number of hypothetical parameters further comprises:
   generating a set of simulated signals using the determined number of hypothetical parameters;
   comparing the measured signal to the set of simulated signals; and
   increasing the number of hypothetical parameters if the measured signal fails to match any of the simulated signals in the set of simulated signals.

15. The method of claim 13, wherein determining the number of hypothetical parameters further comprises:
   generating a set of simulated signals using the determined number of hypothetical parameters;
   comparing the measured signal to the set of simulated signals; and
   decreasing the number of hypothetical parameters until the measured signal fails to match any of the simulated signals in the set of simulated signals.

16. A computer-readable storage medium containing computer-executable instructions to generate simulated diffraction signals of a structure formed on a wafer, comprising instructions for:
   associating hypothetical parameters with a hypothetical profile of the structure to be examined;
   incrementally determining the number of harmonic orders to use in generating simulated diffraction signals;
   generating a simulated diffraction signal using the hypothetical profile and the determined number of harmonic orders; and
   storing the simulated diffraction signal.

17. The computer-readable storage medium of claim 16 wherein incrementally determining the number of harmonic orders comprises instructions for:
   obtaining a measured diffraction signal of the structure;
   generating simulated diffraction signals using increasing number of orders;
   determining the change in the simulated diffraction signals with the increase in the number of orders used; and
   selecting the lower number of orders when the change in the simulated diffraction signals for a pair of consecutive order values is less than the minimum change in the measured diffraction signal that can be obtained.

18. The computer-readable storage medium of claim 16 further comprising instructions for:
   dividing the hypothetical profile into a plurality of hypothetical layers; and
   determining the number of hypothetical layers to use in generating the set of simulated signal for the hypothetical profile.

19. The computer-readable storage medium of claim 18, wherein determining the number of hypothetical layers includes instructions for:
   mapping the determination of the number of hypothetical layers as a set-cover problem; and
   solving the set-cover problem.

20. The computer-readable storage medium of claim 16 further comprising instructions for:
   obtaining a measured diffraction signal of the structure;
   varying the hypothetical parameters within a range to generate a set of hypothetical profiles; and
   adjusting the range to vary the hypothetical parameters based on the measured signal.

21. The computer-readable storage medium of claim 20, wherein adjusting the range to vary the hypothetical parameters includes instructions for:
   generating a set of simulated diffraction signals from the set of hypothetical profiles;
   comparing the simulated diffraction signals of the set and the measured diffraction signal using an error metric; and
   shifting the range to vary the hypothetical parameters when a simulated diffraction signal of the set and the measured signal match and when the hypothetical parameters of the simulated diffraction signal lie near an upper or lower limit of the range.

22. The computer-readable storage medium of claim 16 further comprising instructions for:
   generating a set of simulated diffraction signals from the set of hypothetical profiles;
   determining a resolution for the set of simulated signals; and
   varying the hypothetical parameters used in generating the simulated signals at an increment corresponding to the determined resolution.

23. The computer-readable storage medium of claim 22, wherein the resolution for the parameters is determined based on a desired critical dimension of the periodic grating.

24. The computer-readable storage medium of claim 23, wherein determining the resolution for the parameters further comprises instructions for:
   generating a sub-set of simulated signals including:
      a first-simulated signal generated using a first set of hypothetical parameters, wherein the first set of hypothetical parameters includes:
         a first-hypothetical parameter associated with the desired critical dimension, and
         a second-hypothetical parameter not associated with the desired critical dimension, and
      a second-simulated signal generated using a second set of hypothetical parameters, wherein the second set of hypothetical parameters includes:
         a first-hypothetical parameter matching the first-hypothetical parameter of the first-simulated signal, and
         a second-hypothetical parameter not associated with the desired critical dimension and not matching the second-hypothetical parameter of the first-simulated signal;

removing the second-simulated signal from the sub-set of simulated signals;

comparing the second-simulated signal to the remaining simulated signals in the sub-set of simulated signals; and reducing the resolution to use for the second-hypothetical parameter in generating the set of simulated signals if the comparison matches the second-simulated signal to the first-simulated signal.

25. The computer-readable storage medium of claim 16, wherein associating hypothetical parameters with a hypothetical profile further comprises instructions for:

obtaining a measured diffraction signal of the structure; and determining the number of hypothetical parameters to associate with the hypothetical profile based on the measured signal.

26. The computer-readable storage medium of claim 25, wherein determining the number of hypothetical parameters further comprises instructions for:

generating a set of simulated signals using the determined number of hypothetical parameters;

comparing the measured signal to the set of simulated signals; and increasing the number of hypothetical parameters if the measured signal fails to match any of the simulated signals in the set of simulated signals.

27. The computer-readable storage medium of claim 25, wherein determining the number of hypothetical parameters further comprises instructions for:

generating a set of simulated signals using the determined number of hypothetical parameters;

comparing the measured signal to the set of simulated signals; and decreasing the number of hypothetical parameters until the measured signal fails to match any of the simulated signals in the set of simulated signals.

28. A system for generating simulated diffraction signals of a structure formed on a wafer, the system comprising:

a signal processor configured to:

associate hypothetical parameters with a hypothetical profile of the structure to be examined;

incrementally determine the number of harmonic orders to use in generating simulated diffraction signals;

generate a simulated diffraction signal using the hypothetical profile and the determined number of harmonic orders; and store the simulated diffraction signal.

29. The system of claim 28 further comprising:

a library of simulated diffractions signals, wherein a set of simulated diffraction signals generated using the set of hypothetical profiles is stored.

30. The system of claim 28, further comprising:

an electromagnetic source configured to illuminate the structure with an incident signal; and a detector configured to measure a measured diffraction signal from the incident signal diffracting from the structure, wherein the signal processor is configured to:

obtain the measured diffraction signal of the structure from the detector;

generate simulated diffraction signals using increasing number of orders;

determine the change in the simulated diffraction signals with the increase in the number of orders used; and select the lower number of orders when the change in the simulated diffraction signals for a pair of consecutive order values is less than the minimum change in the measured diffraction signal that can be obtained.

* * * * *